(12) United States Patent
Nayak et al.

(10) Patent No.: US 7,699,803 B2
(45) Date of Patent: Apr. 20, 2010

(54) DEVICES AND METHODS FOR INJECTION OF MULTIPLE-COMPONENT THERAPIES

(75) Inventors: Asha Nayak, Menlo Park, CA (US); Mario Maciel, Pinon Hills, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 143 days.

(21) Appl. No.: 11/969,085

(22) Filed: Jan. 3, 2008

(65) Prior Publication Data

US 2008/0161757 A1    Jul. 3, 2008

Related U.S. Application Data

(60) Provisional application No. 60/878,527, filed on Jan. 3, 2007.

(51) Int. Cl.
*A61M 5/30* (2006.01)
(52) U.S. Cl. .................................................. 604/72
(58) Field of Classification Search .............. 604/82, 604/518, 85, 89–92, 72, 83, 167.05, 173, 604/227, 232, 258, 531
See application file for complete search history.

(56) References Cited

U.S. PATENT DOCUMENTS

| | | | | |
|---|---|---|---|---|
| 3,767,085 A | * | 10/1973 | Cannon et al. ................. 222/82 |
| 4,109,653 A | * | 8/1978 | Kozam et al. ................. 604/191 |
| 4,631,055 A | * | 12/1986 | Redl et al. ..................... 604/82 |
| 4,735,616 A | * | 4/1988 | Eibl et al. ...................... 604/191 |
| 4,753,536 A | * | 6/1988 | Spehar et al. ................. 366/339 |
| 4,823,985 A | | 4/1989 | Grollier et al. |
| 4,874,368 A | * | 10/1989 | Miller et al. ................... 604/82 |
| 5,070,597 A | * | 12/1991 | Holt et al. ...................... 29/887 |
| 5,104,375 A | * | 4/1992 | Wolf et al. ..................... 604/518 |
| 5,582,596 A | * | 12/1996 | Fukunaga et al. ........... 604/191 |
| 5,643,206 A | * | 7/1997 | Fischer ........................ 604/82 |
| 5,935,437 A | * | 8/1999 | Whitmore ................ 210/321.6 |
| 6,132,396 A | * | 10/2000 | Antanavich et al. ........... 604/82 |
| 6,234,994 B1 | * | 5/2001 | Zinger ........................ 604/82 |
| 6,444,228 B1 | | 9/2002 | Baugh et al. |
| 6,605,066 B1 | * | 8/2003 | Gravagna et al. ........... 604/191 |
| 6,610,033 B1 | * | 8/2003 | Melanson et al. ........... 604/181 |

(Continued)

FOREIGN PATENT DOCUMENTS

WO    WO2006/086479    8/2006

(Continued)

*Primary Examiner*—Nicholas D Lucchesi
*Assistant Examiner*—Diva Ranade

(57) ABSTRACT

Devices and methods for injecting or otherwise delivering multiple-component therapies to human or animal subjects. Devices having injectors (e.g., syringes) attached to biaxial or coaxial injection cannula(s) are used to deliver multiple components of a particular therapy such that those components become combined shortly before or upon exiting the injection cannula(s). In some embodiments, the injector devices of the present invention may include a first set of finger grips at a first location and a second set of finger grips at a second location. Also, in some embodiments, the injector devices of the present invention may include depth slops for controlling the depth within tissue at which the therapeutic substance is delivered. Also, in some embodiments, the injector devices of the present invention may include refill manifolds with attached syringes or other reservoirs containing the component substances to facilitate refilling of the injectors.

24 Claims, 8 Drawing Sheets

U.S. PATENT DOCUMENTS

| | | | |
|---|---|---|---|
| 6,732,887 B2 * | 5/2004 | Bills | 222/154 |
| 6,852,099 B2 * | 2/2005 | Redl et al. | 604/289 |
| 6,884,230 B1 * | 4/2005 | Epstein et al. | 604/82 |
| 6,921,381 B2 * | 7/2005 | Spero et al. | 604/82 |
| 6,936,033 B2 * | 8/2005 | McIntosh et al. | 604/191 |
| 6,939,329 B1 * | 9/2005 | Verkaart | 604/191 |
| 6,942,639 B2 | 9/2005 | Baugh et al. | |
| 6,994,686 B2 * | 2/2006 | Cruise et al. | 604/82 |
| 7,081,103 B2 * | 7/2006 | Epstein et al. | 604/82 |
| 7,090,657 B2 * | 8/2006 | Tang | 604/110 |
| 2002/0042591 A1 * | 4/2002 | Muhlbauer et al. | 604/82 |
| 2005/0027240 A1 * | 2/2005 | Fehr et al. | 604/82 |
| 2005/0182357 A1 * | 8/2005 | Snell et al. | 604/82 |
| 2005/0209564 A1 | 9/2005 | Bonner et al. | |
| 2006/0041242 A1 | 2/2006 | Stypulkowski | |
| 2006/0184102 A1 * | 8/2006 | Trombley et al. | 604/82 |
| 2006/0253082 A1 * | 11/2006 | McIntosh et al. | 604/191 |
| 2007/0014784 A1 | 1/2007 | Nayak et al. | |
| 2008/0167621 A1 * | 7/2008 | Wagner et al. | 604/191 |

FOREIGN PATENT DOCUMENTS

| | | |
|---|---|---|
| WO | WO2007/089948 | 8/2007 |
| WO | WO2007/112135 | 10/2007 |

* cited by examiner

DEVICES AND METHODS FOR INJECTION OF MULTIPLE-COMPONENT THERAPIES

RELATED APPLICATION

This patent application claims priority to U.S. Provisional Patent Application No. 60/878,527 filed Jan. 3, 2007.

FIELD OF THE INVENTION

The present invention relates generally to medical devices and methods, and more particularly to devices and methods for injecting or otherwise delivering multiple-component therapies to human or animal subjects.

BACKGROUND

It is sometimes desirable to deliver (e.g., inject, infuse, apply, etc) two or more chemical substances to a desired location within the body of a human or animal subject such that the substances become combined or mixed shortly before, during or shortly after delivery into the body. For example, some therapies involve the administration of two or more component substances (e.g., chemical compounds, solutions, suspensions, biologics, cells, reactants, etc.) such that those substances react or otherwise interact with each other to form a resultant mixture or reaction product that directly or indirectly results in some therapeutic, diagnostic or cosmetic benefit (generally referred to herein as "Multiple-Component Therapies"). In some cases, it is important for the component substances to be combined or mixed immediately before, during or after delivery. This is the case, for example, when mixing or combining of the component substances too long before delivery would result in an increase in viscosity or solidification process that would render the product incapable of passing through an intended delivery cannula or needle or where the product has a very short half life and would loose activity before reaching its intended in vivo destination.

One Multiple Component Therapy is known as platelet gel (PG). In this therapy, a platelet-containing component (e.g., platelet rich plasma (PRP)) is combined with a thrombin-containing component (e.g, a thrombin solution) immediately before, during or after injection into the myocardium at one or more location(s) within or near an infarct or other myocardial injury. The platelet-containing component (e.g., PRP) combines with the thrombin-containing component and forms a platelet gel (PG) which causes the desired therapeutic effect. Such PG is formed when components (such as fibrinogen) contained in the platelet-containing component are activated by thrombin contained in the thrombin-containing component. Autologous PRP can be obtained from the subject's own blood, thereby significantly reducing the risk of adverse reactions or infection. When autologous PRP is used as the platelet-containing component, the resultant PG is referred to as autologous platelet gel (APG). The addition of thrombin to platelet-containing plasma products such as PRP is described in detail in U.S. Pat. No. 6,444,228, the disclosure of which is expressly incorporated herein by reference. PRP has also been used in a variety of orthopedic and other applications.

Moreover, the preparation and use of PG and APG for improving cardiac function and/or preventing deleterious ventricular remodeling following myocardial infarction or other injury to the myocardium is being investigated by Medtronic Vascular, Inc. of Santa Rosa, Calif., as described in parent U.S. patent application Ser. No. 11/426,219 (published as 2007-0014784) and in United States Patent Application Publication Nos. 2006/0041242 and 2005/209564, the entire disclosures of which are expressly incorporated herein by reference. Since it may be difficult to pass PG or APG through the lumen of a needle, it is desirable to inject the platelet-containing component and the thrombin-containing component such that they become mixed immediately prior to, during or after injection through the needle. Additionally, injecting the platelet-containing component and the thrombin-containing component separately or immediately after mixing may allow the infusate to distribute to a greater area before fully gelling into the PG or APG, thereby possibly enhancing the effect of this therapy.

Other examples of Multiple Component Therapies known in the prior art include, but are not limited to; multiple component tissue adhesives and sealants (e.g., Tisseel VH™ Fibrin Sealant, available commercially from Baxter Healthcare Corporation, Deerfield, Ill.); tissue bulking agents, fillers or polymeric materials (e.g., hydrogels) that may be formed or expanded in situ for various therapeutic or cosmetic applications such as tissue bulking, filling or expanding and various prodrug+activator combinations.

The prior art has also included a number of injector assemblies that may be usable for delivering Multiple Component Therapies. For example, U.S. Pat. No. 4,823,985 (Grollier, et al.) describes a dispensing assembly usable for dispensing at least two constituents such that the constituents become mixed to form a homogenous product. This dispensing assembly has flexible walls and at least two compartments, including outlet orifices located adjacent to one another so that when the outlet orifices are opened as by cutting, and pressure is applied to the flexible walls, dispensing and immediate mixing of the constituents will be effected; the viscosity and volumes of the constituents are selected to have certain values to enable the dispensing to properly mix the constituents to form a homogenous product. The dispensing assemblies described in U.S. Pat. No. 4,823,985 (Grollier et al.) do not include any needle having a tissue penetrating tip or other means for injecting the constituents into tissue.

U.S. Pat. No. 6,936,033 (McIntosh, et al.) describes a double syringe system for holding a pair of syringes in a manner so as to accommodate the simultaneous activation of the plunger of each syringe in order to effect simultaneous delivery of the contents of each syringe. The delivery system includes a support member that is positioned between the two syringe bodies. The elongated support member has resilient, C-shaped clamps on one end of the support member. The clamps are designed to be removably clamped onto the applicator so that the syringe barrels will be held together in a parallel manner. The elongated support member further comprises finger grips. A plunger connects the two syringe plungers so that they can also be simultaneously activated. Two side-by-side cannulas extend from the distal end of the delivery system and, as the plungers are depressed, the material from one syringe flows through one cannula and the material from the other syringe flows through the other cannula. The distal ends of the cannulas are aligned with each other so that there will be simultaneous delivery of the separated fluids from both syringes to the application site. In one embodiment, the side-by-side cannulas comprise needles of substantially equal length. Each of these needles bent towards each other so that as the needles approach their distal ends, they run parallel to each other and touch. The parallel portions of needles can be joined together with a sleeve, adhesive, or other methods known in the art. In another embodiment, the cannulas are formed of flexible lengths of tubing that are cut off at equivalent lengths and attached at their distal ends, usually with solvent adhesive. In yet another embodiment, the delivery system has a delivery tip that comprises a hollowed double fluid path attached to a single cannula fitting such as that described in U.S. Pat. No. 5,104,375, which is specifically incorporated herein by reference. Alternatively, the delivery system may have spray heads attached to each syringe.

U.S. Pat. No. 6,942,639 (Baugh et al.) describes a system for delivering and combining an activated blood component and an inactivated blood component, which combine to form APG. This system comprises separate chambers which contain the activated blood component and the inactivated blood component, respectively. The first chamber includes an activating agent and a filter (which may be one and the same) which causes a clot (which forms in the blood component) to become triturated, thereby isolating thrombin from the clot. The second chamber stores the inactivated blood component (e.g., PRP) that, when mixed with thrombin, produces a gel. The first or second chamber may further contain agents which are desired to be delivered to a specific site. The design of the delivery system allows for ease in operation of combining two agents at a specific time and place.

United States Published Patent Application 2006/0253082 describes dispensing systems and methods for dispensing platelet gel or other two component treatments. These dispensing systems include a handle assembly that is designed to hold two syringes and thumb plate that is used to depress the plungers of both syringes simultaneously. The fluids contained in the separate syringes then flow through separate channels in a manifold and through a tip assembly. In various embodiments the tip assembly may include specialized various nozzles that entrain non-atomized flow of a first fluid in an atomized flow of a second fluid, delivering a first fluid upstream from a second fluid, delivering a first fluid and a second fluid with re-shapeable malleable tubes, delivering first and second fluids with releasable connectors maintained by a handle assembly.

There remains a need for the development of new devices and methods for injecting platelet gel or other Multiple Component Therapies to selected locations within the bodies of human or animal subjects such that the component substances become mixed or combined immediately before, during or after delivery into or onto the body of the subject.

SUMMARY OF THE INVENTION

The present invention provides new devices and methods for administering Multiple Component Therapies such that the component substances become combined immediately before, during or after delivery into or onto the body of a human or animal subject.

In accordance with the invention, there is provided a device for administering a plurality of component substances into or onto the body of a human or animal subject such that the component substances become combined to produce a resultant component mixture or reaction product that directly or indirectly results in some therapeutic, diagnostic or cosmetic benefit. Such device generally comprises a) a manifold having a first component substance flow channel and a second component substance flow channel; b) a first injector connectable to the manifold and usable to inject a first component substance into the first component substance flow channel of the manifold; c) a second injector connectable to the manifold and usable to inject a second component substance into the second component substance flow channel of the manifold and d) an injector cannula assembly comprising i) an outer tube that has an outer tube lumen and a distal opening, said outer tube being connected to the first component substance flow channel of the manifold such that the first component substance will flow through the outer tube lumen and ii) an inner tube that has an inner tube lumen and a distal opening, said inner tube being connected to the second component substance flow channel of the manifold such that the second component substance will flow therefrom into the inner tube lumen and out of the distal opening of the inner tube. At least a portion of the inner tube extends through at least a portion of the outer tube lumen such that the second component substance flowing out of the distal opening of the inner tube becomes combined with the first component substance that flows through the lumen of the outer tube thereby forming a resultant component substance mixture or reaction product.

Further in accordance with the present invention, there is provided a method for administering a plurality of component substances into or onto the body of a human or animal subject such that the component substances become combined to produce a resultant mixture or reaction product that directly or indirectly results in some therapeutic, diagnostic or cosmetic benefit. Such method generally comprises the steps of: a) providing a device which comprises i) a manifold having a first component substance flow channel and a second component substance flow channel, ii) a first injector connectable to the manifold and usable to inject a first component substance into the first component substance flow channel of the manifold, iii) a second injector connectable to the manifold and usable to inject a second component substance into the second component substance flow channel of the manifold and iv) an injector cannula assembly that includes an outer tube that has an outer tube lumen and a distal opening, said outer tube being connected to the first component substance flow channel of the manifold such that the first component substance will flow through the outer tube lumen and an inner tube that has an inner tube lumen and a distal opening, said inner tube being connected to the second component substance flow channel of the manifold such that the second component substance will flow therefrom into the inner tube lumen and out of the distal opening of the inner tube, wherein at least a portion of the inner tube extends through at least a portion of the outer tube lumen such that the second component substance flowing out of the distal opening of the inner tube becomes combined with the first component substance that flows through the lumen of the outer tube thereby forming a resultant component substance mixture or reaction product; b) attaching injectors to the manifold, c) positioning the injector cannula at a desired location within or on the subject's body and d) using the injectors to inject component substances through the manifold and through the at least one injector cannula such that the resultant component substance mixture or reaction product is deposited at a desired location in or on the subject's body.

Still further in accordance with the present invention, there is provided an injector device which generally comprises a) at least one injector having a barrel into which a flowable substance may be loaded, an outlet opening and a plunger that may be depressed by the thumb of a user to cause a substance that has been loaded into the barrel to be expelled out of the outlet opening, b) a first set of finger grips at a first location and c) a second set of finger grips at a second location.

Still further in accordance with the present invention, there is provided a method for administering at least one substance into or onto the body of a human or animal subject. Such method generally comprises the steps of a) providing a device which comprises i) at least one injector having a barrel into which a substance may be loaded, an outlet opening and a plunger that may be depressed to cause a substance that has been loaded into the barrel to be expelled out of the outlet opening, ii) a first set of finger grips at a first location and iii) a second set of finger grips at a second location, b) loading a substance into the barrel, c) selecting either the first set of finger grips or the second set of finger grips, d) placing fingers of one hand under the finger grips selected in Step B, e) placing the thumb of the same hand in a position to depress the plunger and f) using the thumb to depress the plunger thereby expelling at least some of the substance from the barrel and out of the outlet opening.

Further or alternative elements, aspects, objects and advantages of the present invention will be understood by those of skill in the art upon studying of the accompanying drawings and reading of the detailed description and examples set forth below.

DETAILED DESCRIPTION AND EXAMPLES

Figure 1A:
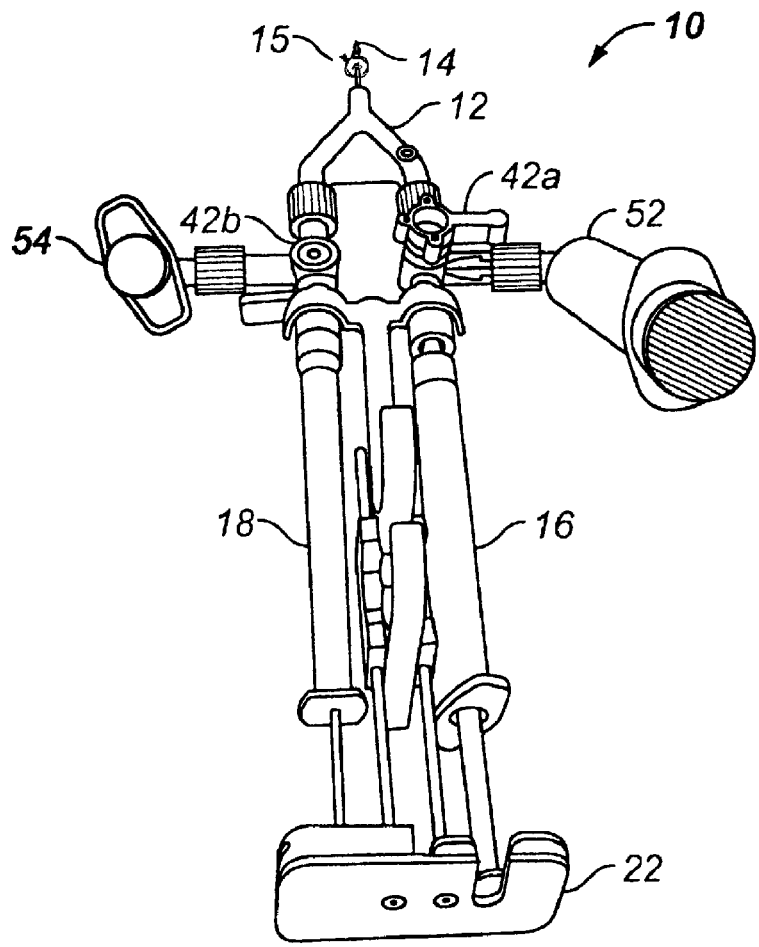
FIG. 1A is a top perspective view of one embodiment of a Multiple Component Therapy delivery device of the present invention.

The following detailed description and the accompanying drawings are intended to describe some, but not necessarily all, examples or embodiments of the invention. The contents of this detailed description and accompanying drawings do not limit the scope of the invention in any way.

With reference to FIGS. 1A-2B, one embodiment of a Multiple Component Therapy delivery device 10 of the present invention generally comprises a manifold 12 having a coaxial injector cannula 14 extending distally therefrom, an optional fill reservoir assembly 40 that is attached to the manifold 12, component substance injectors (e.g., syringes) 16, 18 (or alternatively other types of injectors for infusing or injecting the component substances) and a handle/injection control assembly 20. The manifold 12 may be formed of molded plastic or otherwise constructed of materials that are compatible with the component substances that are to be infused therethrough. The coaxial injector cannula 14 of this embodiment may, in some embodiments, have a sharp distal end suitable for advancement through tissues of the body or may have blunt distal end(s) suitable, for example, for topical application or for advancement into the body through an existing opening (e.g., a natural or man made orifice, opening, incision, port, introducer, trocar or the like).

One use that is contemplated for the current invention is to deliver multi component therapeutic substances into a heart. Access to the heart can be achieved via an open chest surgical procedure, through the walls of the chest during a minimally invasive surgical procedure, or via a percutaneous injection while using suitable imaging techniques to ensure delivery to the appropriate location.

Those of skill in the art will appreciate that the device 10 may be used to deliver a variety of Multiple Component Therapies by any desired routes of administration, including but not limited to topical routes (e.g., epicutaneous, epimucosal, epiconjunctival or by delivery onto internal body surfaces through nasal, oral, rectal, vaginal, urethral or other administration), enteral routes (oral, rectal, by gastric tube or other introduction for absorption via the gastrointestinal tract) and/or parenteral routes (e.g., intramuscular, intravenous, intraarterial, intrathecal, subcutaneous, intraosseous, intradermal, intraperitoneal, intravitreal, intracardiac, etc.)

In use, the device 10 may be use to inject or deliver a desired Multiple Component Therapy. In the particular embodiment shown in FIGS. 1A-2A, the component substances are expelled from the component injectors 16, 18 and flow through separate flow channels 28, 30 within the manifold 12. As may be appreciated from the enlarged views of FIGS. 2A and 2B, in embodiments which incorporate the coaxial injection cannula 14, the first component substance flows from one channel 28 of manifold 12 into a first injection cannula 70 and the second component substance flows from the other channel 30 of the manifold 12 into a second injection cannula 72. In the depicted embodiment, the first injection cannula 70 is shorter than the second injection cannula 72. For example, in some embodiments, the first injection cannula may extend approximately 3 mm out of the manifold 12 and the second injection cannula 72 may extend out of the manifold 12. The first and second injection cannulas 70, 72 may be formed or any suitable material, such as stainless steel hypotube of a size that is appropriate for the intended application. For example, in devices 10 intended for use in injecting APG into myocardial tissue, a stainless steel hypotube of about 24 gauge to about 28 gauge and typically about 26 gauge, may be used. A side opening 77 is formed in the second injection cannula 72 some distance distal to the end of the first injector cannula 70. A tube 76, such as a flexible plastic tube, is connected to the first injection cannula and extends through side opening 77 and into the lumen 79 of second injection cannula 72, as shown in FIG. 2A. The tube 76 extends distally through the lumen 79 of the second injector cannula 72 to a position where the distal end 78 of the tube 76 is a desired distance $D_1$ from the open distal end 74 of the second injector cannula 72. The tube 76 has an outer diameter that is smaller than the inner diameter of the second injection cannula 72. The first component substance flows from the first injector cannula 70, through tube 76 and out of the distal end of tube 78. The second component substance flows through the lumen 79 of the second injector cannula 72 and around the portion of tube 76 that resides within lumen 79 such that the first and second component substances become combined to form a resultant component mixture or reaction product.

This distance $D_1$ between the distal end 78 of the tube 76 and the distal end 74 of the second injector cannula 72 may vary, depending on the type of Multiple Component Therapy being delivered. For example, in some embodiments the distal end 78 of the tube 76 may be substantially flush with the distal end 76 of second injector cannula 72 (i.e., $D_1=0$) such that the first and second component substances remain separate and do not become mixed until they exit the distal end 74 of the second injection cannula 72. In other embodiments, the distal end 78 of the tube 76 may be some distance proximal to the distal end 76 of second injector cannula 72 (i.e., $D_1>0$) such that the first and second component substances become mixed while in the lumen 79 of the second injection cannula 72 and the resultant component mixture or reaction product will be formed before it flows out of the distal end 74 of the second injection cannula 72.

In at least one embodiment that is not depicted, the distal end of the tube that comprises the first injection cannula extends beyond the distal end of the second injection cannula and the distal ends of both the first injection cannula and the second injection cannula are beveled. In such an embodiment, the tube that comprises the first injection cannula is made from a material that will provide the necessary rigidity for delivering an injectate into a desired tissue (e.g. a stainless steel hypotube). This embodiment allows delivery of separate components at different depths in the tissue relative to each other. In some instances where separate components are delivered to different depths relative to each other, the components combine with each other in the tissue after the injection device has been withdrawn.

In general, this coaxial injector 14 embodiment may be useful for delivering Multiple Component Therapies where it is desired to keep the component substances separate until they exit the injector or just prior to their exit from the injector. Such may be desirable in situations where the resultant component mixture or reaction product undergoes a rapid chemical reaction, a rapid change in state, a rapid increase in viscosity, has a very short active life or otherwise must be administered immediately or very shortly after the component substances have become combined or mixed.

It will be appreciated by those of skill in the art that the specific construction of the coaxial injector cannula 14 shown in the figures is merely an example and other alternative modes of construction may be employed to achieve the desired result. For example, in some embodiments, the manifold 12 may be designed such that the first and second flow channels 28, 30 become merged within manifold 12 and the resultant component mixture or reaction product then flows through a single lumen (e.g., a single injection cannula) that extends from the manifold 12.

Figure 2:
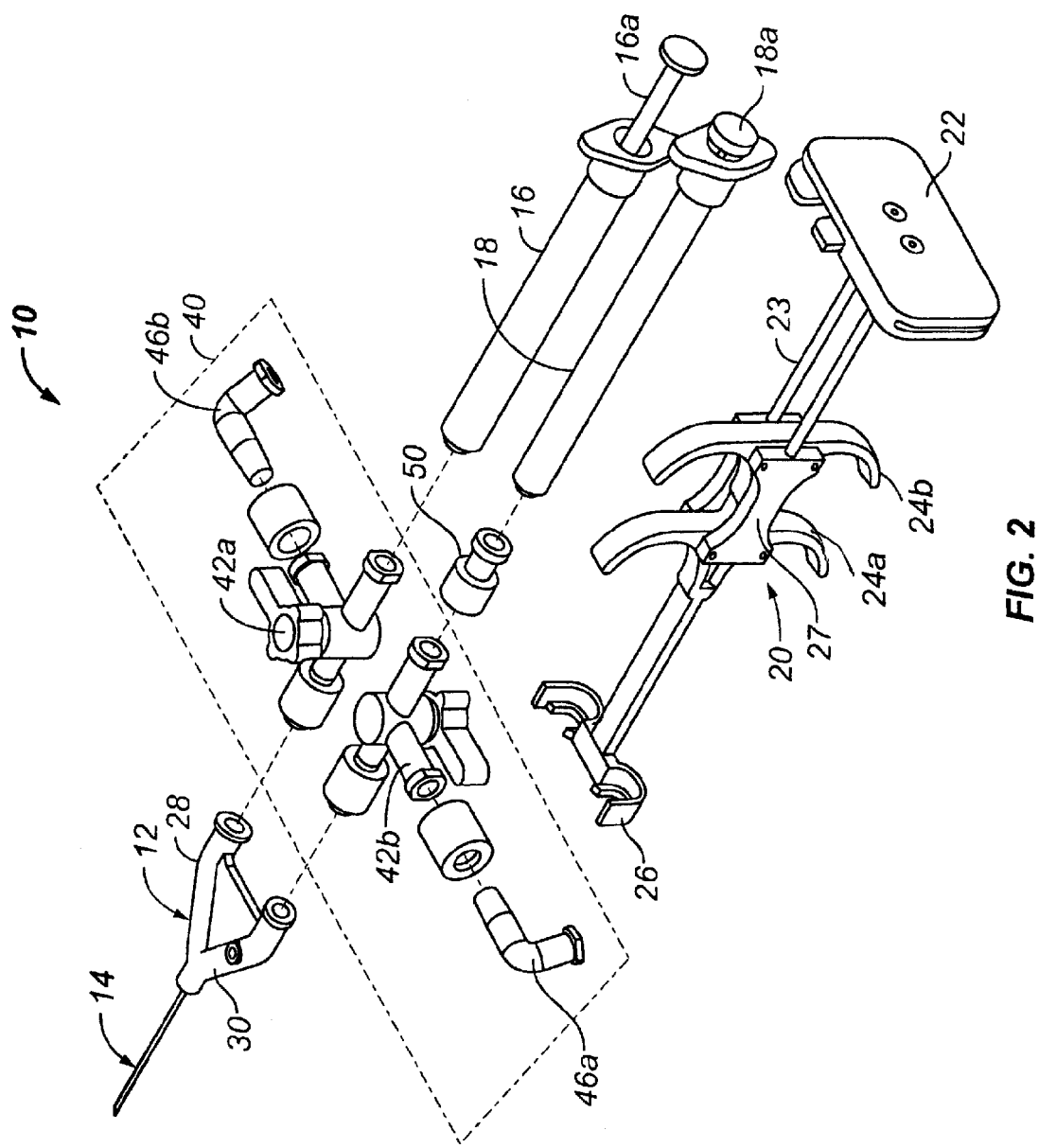
FIG. 2 is an exploded view of the device of FIG. 1A.
Figure 2A:
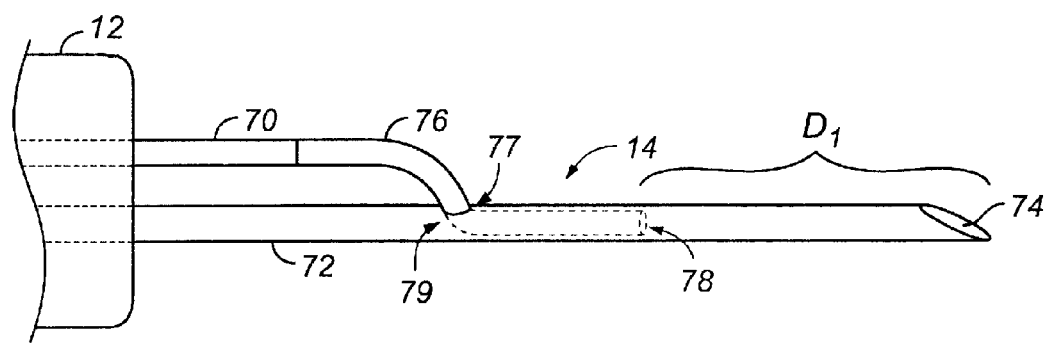
FIG. 2A is an enlarged side view of the coaxial injector cannula of the device of FIG. 1A.
Figure 2B:
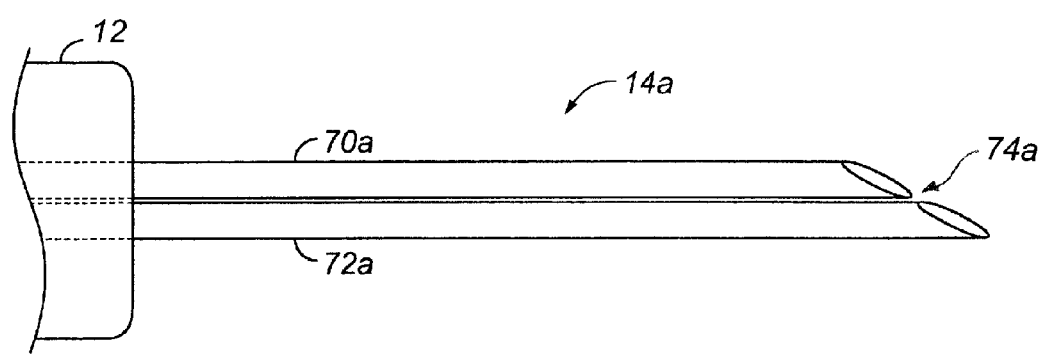
FIG. 2B is an enlarged side view of an alternative biaxial injector cannula that may be incorporated in the device of FIG. 1A.
Figure 3:
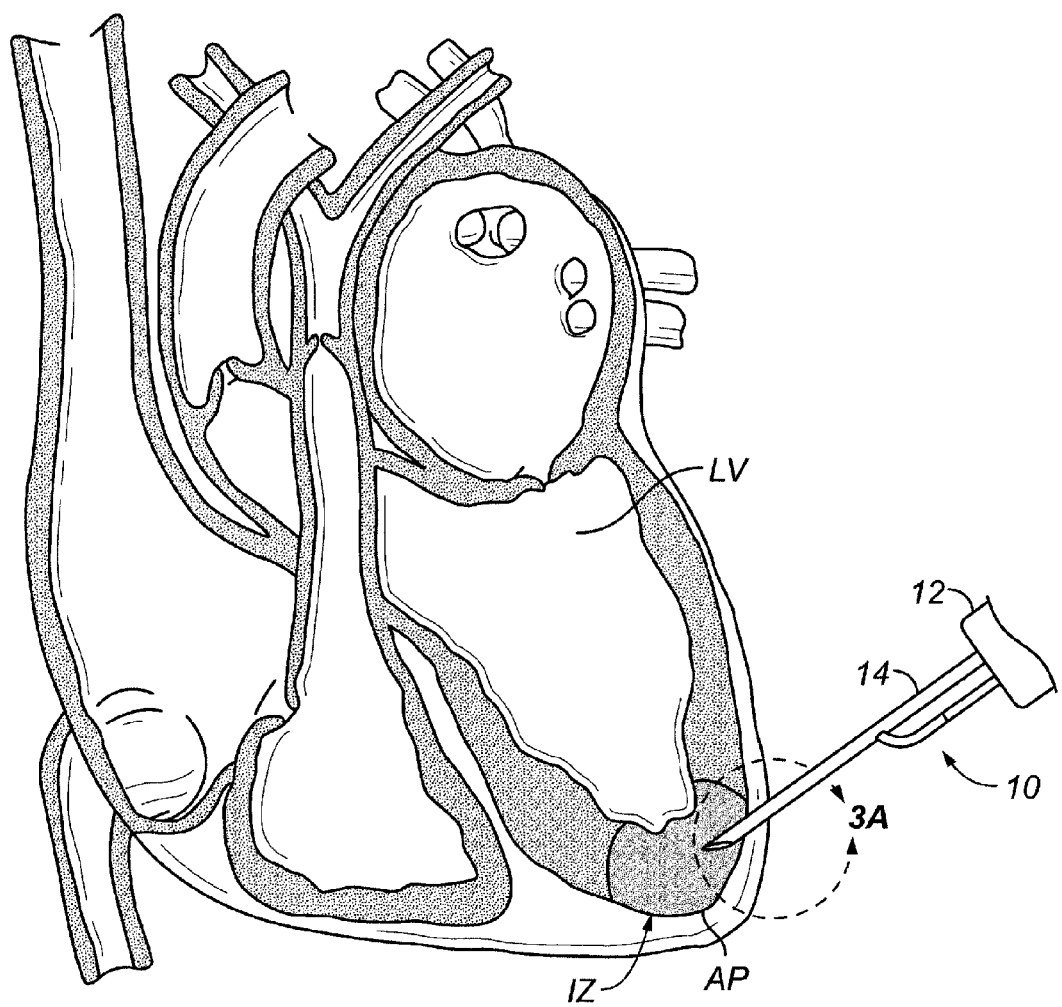
FIG. 3 is a diagram showing a sagittal section of a human heart with a device of the present invention being used to inject APG into a myocardial infarct zone located the anterior wall of the left ventricle near the apex of the heart.
Figure 3A:
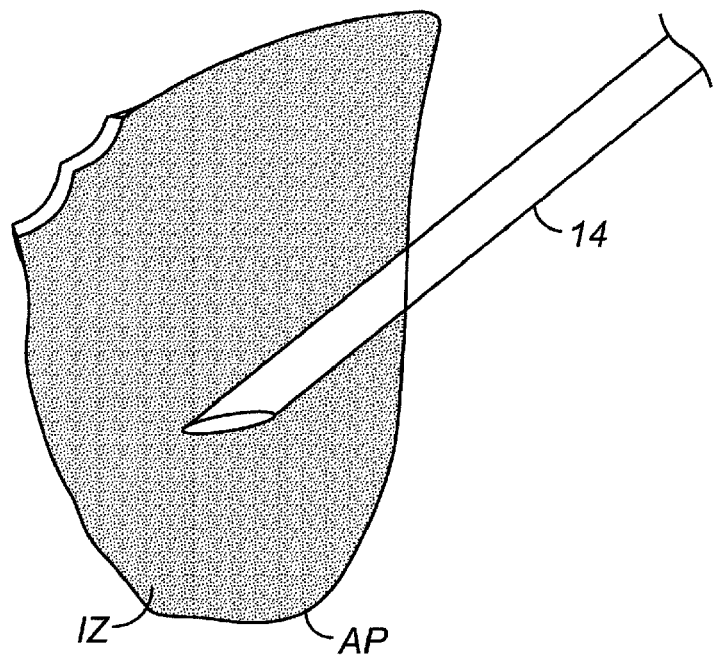
FIG. 3A is an enlarged view of section 3A of FIG. 3.

FIG. 2B shows the distal portion of a biaxial injection cannula 14a wherein a first injection cannula 70a and second injection cannula 72a extend in side by side fashion. A sharp, beveled distal end 74a may be formed at the distal ends of these injection cannulas 70a, 72a. In this embodiment, one component substance flows through the lumen 71 of the first injection cannula 70a and a second component substance flows through the lumen 79a of the second injection cannula 72a Such biaxial lumens 71, 79a are sufficiently close-spaced that, as the separate streams of component substances flow out of the distal ends of these cannulas 70a, 72a, they will become combined (e.g., they may pool together within tissue or on a surface of the subject's body) thus resulting in situ formation of the resultant component combination or reaction product. In such embodiments, the biaxial lumens may be of differing or equal lengths. In the particular example shown the first injection cannula 70a is only slightly shorter than the second injection cannula 72a due to the nature of the bevel cut at the distal end 74a. Having a bevel cut at the distal end of the biaxial injector cannula 14a or coaxial injector cannula 14 may be useful in applications where it is desired to deliver the Multiple Component Therapy to a location that is adjacent to one side or the other of the injection cannula tip, such as within the myocardium near the apex of the heart when the needle is advanced at an inferior angle such that the apex is located to one side of the needle as seen in FIGS. 3 and 3A.

As shown in FIGS. 1A and 2, when the three way stopcocks 42a, 42b (or other suitable valves) of the optional fill reservoir assembly 40 are attached to manifold 12 and component injector syringes 16, 18 as well as fill reservoirs (e.g., syringes that are larger than the corresponding injector syringes) are attached to separate side arms of valves such as three way stopcocks 42a, 42b. These stopcocks 42a, 42b may be alternately placed in a first position that allows component substance material to be withdrawn from fill syringe 52 through elbow 46b into delivery syringe 16 and from fill syringe 54 through elbow 46a into delivery syringe 18. Thereafter, the stopcocks 42a, 42b may be moved to a second position that allows the component substances to be injected from component substance syringes 16, 18, through manifold 12 and through the delivery cannula(s) or needle(s) 14, 14a. This may be repeated one or more times, thus allowing the component substance syringes 16, 18 to be refilled and used to deliver repeated doses or injections of the Multiple Component Therapy without requiring that the component substance syringes 16, 18 be removed or detached from the device 10. It is to be appreciated that, although the drawings show the use of fill syringes 52, 54 as the fill reservoirs, various other types of reservoirs may be used instead of syringes. For example, compliant reservoirs, such as flexible vessels or plastic bags, may be filled with the component substances and connected to the appropriate side arms of stopcocks 42a, 42b and may function as fill reservoirs instead of the fill syringes 52, 54 shown in the drawings.

The device 10 also may include an optional handle/injection control assembly 20 which facilitates handling of the device 10 as well as simultaneous depression and/or withdrawal of the plungers 16a, 18a of component injector syringes 16, 18. The component injector syringes 16, 18 are mounted in syringe mounting brackets 26 with two sets of finger grips 24a, 24b protruding between the syringes 16, 18. One set of finger grips 24a is located distal to the other set of finger grips 24b, thereby allowing users having different sized hands to select the finger grip set 24a, 24b that is best suited from them. The thumb pads located on the ends of syringe plungers 16a, 18a are received in slots formed on a depressible member such as thumb plate 22. Rods 23 slide back and forth in bores formed in body member 27. Thus, when filling the syringes 16, 18, the stopcocks 42a, 42b are placed in their first positions and the syringe plungers 16a, 18a are simultaneously retracted by pulling the thumb plate 22 in the proximal direction. It will be appreciated that, in some embodiments, instead of including two or more sets of finger grips 24a, 24b at longitudinally spaced apart locations, a single set of longitudinally adjustable finger grips 24a may be provided such that the operator may adjust the position of those finger grips thereby setting the distance between that adjustable set of finger grips and the thumb plate 22 to optimize comfort and ease of use for that operator.

It will be further appreciated that, in some applications, both component injector syringes 16, 18 may be of substantially the same length and/or size while in other applications the component injector syringes 16, 18 may be of substantially different length or size. In applications where one of the component injector syringes 16, 18 is shorter than the other, the shorter syringe may be attached to the proximal end of an optional spacer 50 (e.g., a straight male-female Luer fitting) and the distal end of that spacer 50 may be attached to the adjacent stopcock 42a or 42b. In this manner, by selecting a spacer 50 of the proper length, the component injector syringes 16, 18 will be appropriately positioned such that their plunger thumb pads 16a, 18a will insert into the respective slots on thumb plate 22 and their plungers 16a, 18a will advance concurrently with advancement of the thumb plate 22 to expel the intended amounts of the component substances, despite differences in the lengths of the component injector syringes 16, 18. Use of this optional spacer 50 may be particularly advantageous in applications where the intended component substance mix ratio requires delivery of a comparatively large volume of one component substance and a comparatively small volume of another component substance.

Figure 4:
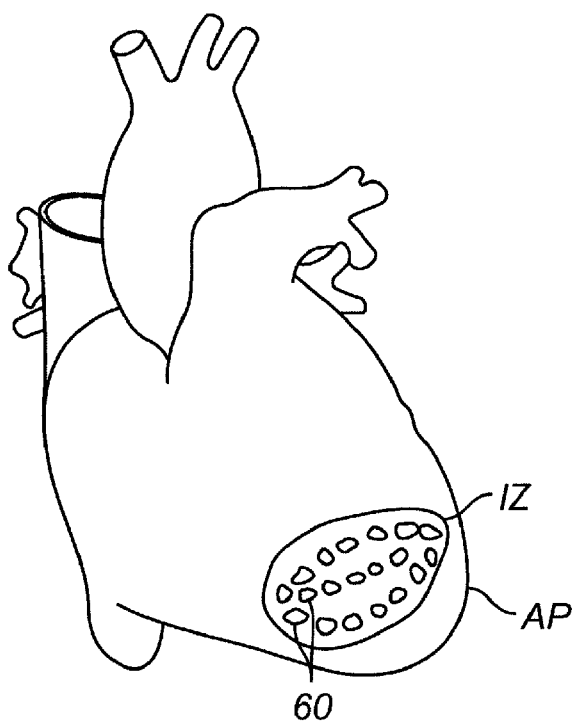
FIG. 4 is a diagram of a human heart with an infarct of the anterior left ventricular wall showing one example of locations at which APG can be injected into the myocardium to treat impaired myocardial function resulting from the infarct.
Figure 5:
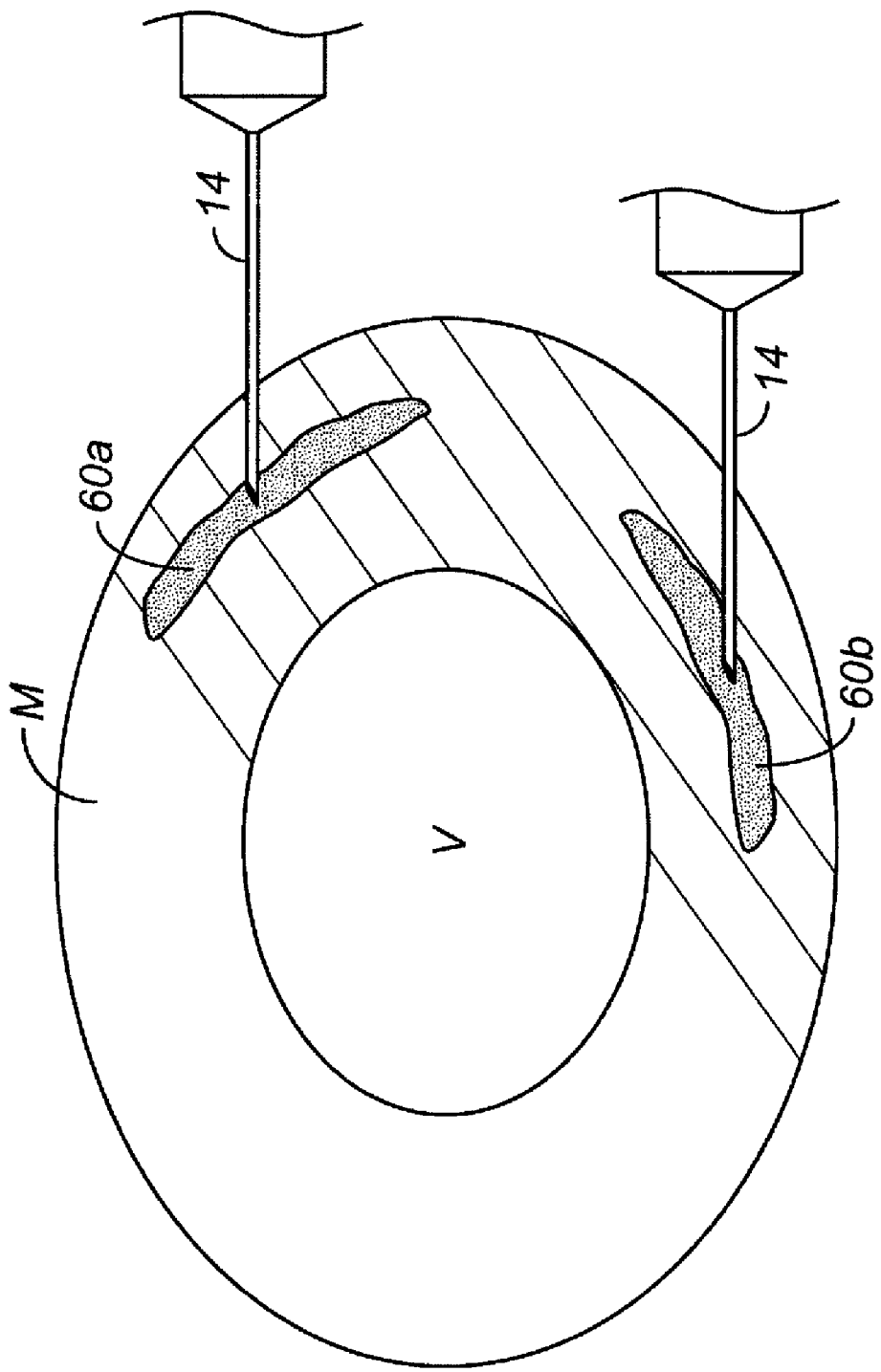
FIG. 5 is a schematic, cross sectional diagram of a portion of a human heart showing a device of the present invention being used to inject deposits of a Multiple Component Therapy at selected locations within a ventricle wall.

After the component injector syringes 16, 18 have been filled with the component materials, the stopcocks 42a, 42b are moved to their second positions. The injector cannula(s) 14,14a is/are inserted into the subject's body or positioned adjacent to an area on the subject's body to which the Multiple Component Therapy is to be delivered. As shown in the drawings, in some embodiments, the injector cannula(s) 14,14a may have beveled or otherwise sharp tips capable of penetrating through tissue and the procedure may involve advancing the injector cannula(s) 14,14a through tissue to a desired location where the Multiple Component Therapy is to be delivered. Specific examples of this are shown in FIGS. 3-5 and are described in detail herebelow.

Alternatively, for some applications, the injector cannula (s) 14,14a may have blunt tips. Examples of application where blunt tipped injector cannula(s) 14,14a may be used include but are not necessarily limited to those in which the Multiple Component Therapy is to be delivered topically onto a body surface or through an existing body orifice or opening (e.g., intranasal, rectal, vaginal, etc.) such that it is not necessary for the distal ends of the injector cannula(s) 14,14a to penetrate through tissue.

After the injector cannula(s) 14,14a have been positioned at the desired location, the operator's fingers are inserted under the selected set of finger grips 24a, 24b and the operator's thumb is placed on thumb plate 22. Thumb pressure is then applied to advance thumb plate 22 in the distal direction, thereby depressing syringe plungers 16a, 16b simultaneously at substantially the same rate. This causes the component substances to flow through manifold 12 and through the delivery cannula(s) or needle(s) 14 and causes the resultant combination material to be delivered onto or into the subject's body as described herein.

Figure 1B:
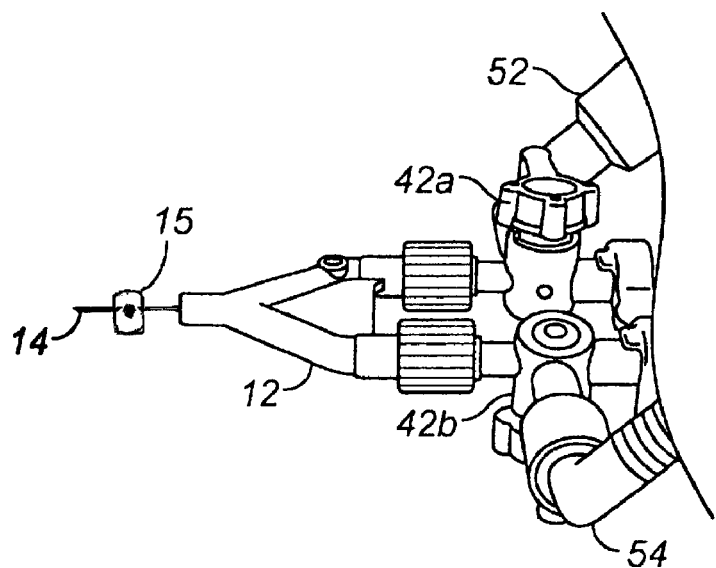
FIG. 1B is an enlarged view of a distal portion of the device of FIG. 1A
Figure 7:
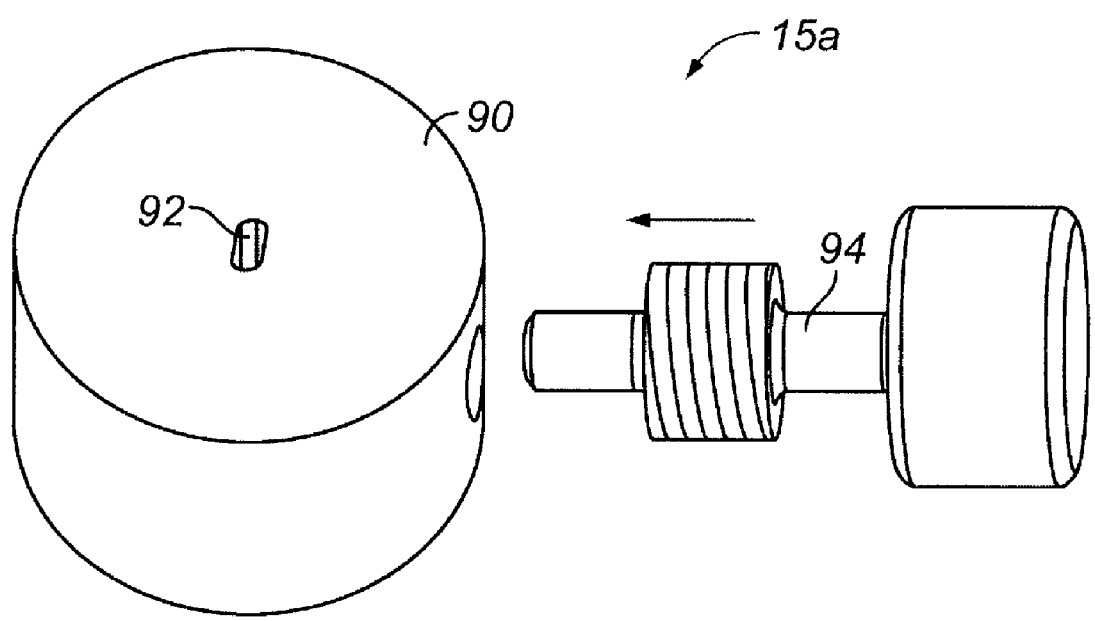
FIG. 7 is an exploded view of an optional depth stop device that may be used to control the depth at which a substance is delivered into tissue using the devices and methods of the present invention.

As seen in FIGS. 1A, 1B and 7, an optional depth stop 15, 15a may be formed on, attached to or positioned adjacent the delivery cannula(s) or needle(s) 14, 14a to limit the depth to which the delivery cannula(s) or needle(s) 14, 14a may be advanced into tissue. Such depth stop 15, 15a may comprise an enlarged diameter area or projections formed on the outer surface(s) of the delivery cannula(s) or needle(s) 14, 14a or may comprise a separate device that is attached to the delivery cannula(s) or needle(s) 14, 14a, an example of which is shown in FIG. 7. The depth stop device 15a seen in FIG. 7 comprises an abutment member 90 having an aperture 92 through which the delivery cannula(s) or needle(s) 14, 14a may be advanced and a tightening member 94, such as a set screw, which frictionally engages the delivery cannula(s) or needle(s) 14, 14a and holds the abutment member 90 at the desired location on the delivery cannula(s) or needle(s) 14, 14a. In this manner, the delivery cannula(s) or needle(s) 14, 14a may be advanced into tissue only until the abutment member 90 abuts against the surface of the tissue (e.g., the epicardial surface of the heart, organ or other anatomical structure) thereby controlling the depth at which the substance will be injected.

In another embodiment of depth stop (not shown) the surface of the abutment member that makes contact with the surface of the tissue is beveled. The angle of the bevel can be set at an angle that will allow the distal tip of the cannula(s) or needle(s) to penetrate the tissue at a desired angle (for example an injection toward the apex of a heart).

It will be appreciated that the devices and methods of this invention may be used to deliver many types of Multiple Component Therapies. As seen in FIGS. 3-5, in one particular type of Multiple Component Therapy, the component substances comprise a platelet-containing component (e.g., PRP or autologous PRP) and a thrombin-containing component (e.g., a thrombin solution) and the resultant combination material is PG or APG. The PG or APG is delivered to selected sites within the myocardium to deter negative remodeling of the ventricular wall or to otherwise improve myocardial function as described in U.S. patent application Ser. No. 11/426, 219 (published as 2007-0014784) and in United States Published Patent Application Nos. 2006/0041242 and 2005/ 209564, the entire disclosures of which are expressly incorporated herein by reference. This is illustrated in the schematic diagram of FIGS. 3-5 wherein the coaxial injector cannula 14 is shown to be inserted into myocardial tissue within or near an infarct zone IZ that is located in the myocardial wall of the left ventricle LV near the apex AP of the heart. In some applications, a single injection of the Multiple Component Therapy may be sufficient. In other applications, the injector cannula 14 may be withdrawn and reinserted at a number of locations and a deposit 60a, 60b of APG+thrombin solution will be deposited at each such location within the myocardium M, without penetrating into the ventricle adjacent ventricle. The locations at which the deposits 60a, 60b are deposited may form a pattern within and/or adjacent to an infarct zone IZ as shown, for example, by deposits 60 in FIG. 4. Injections may be made into normal, injured, or diseased tissue, depending on the type of substance being delivered and its intended effect.

Figure 6:
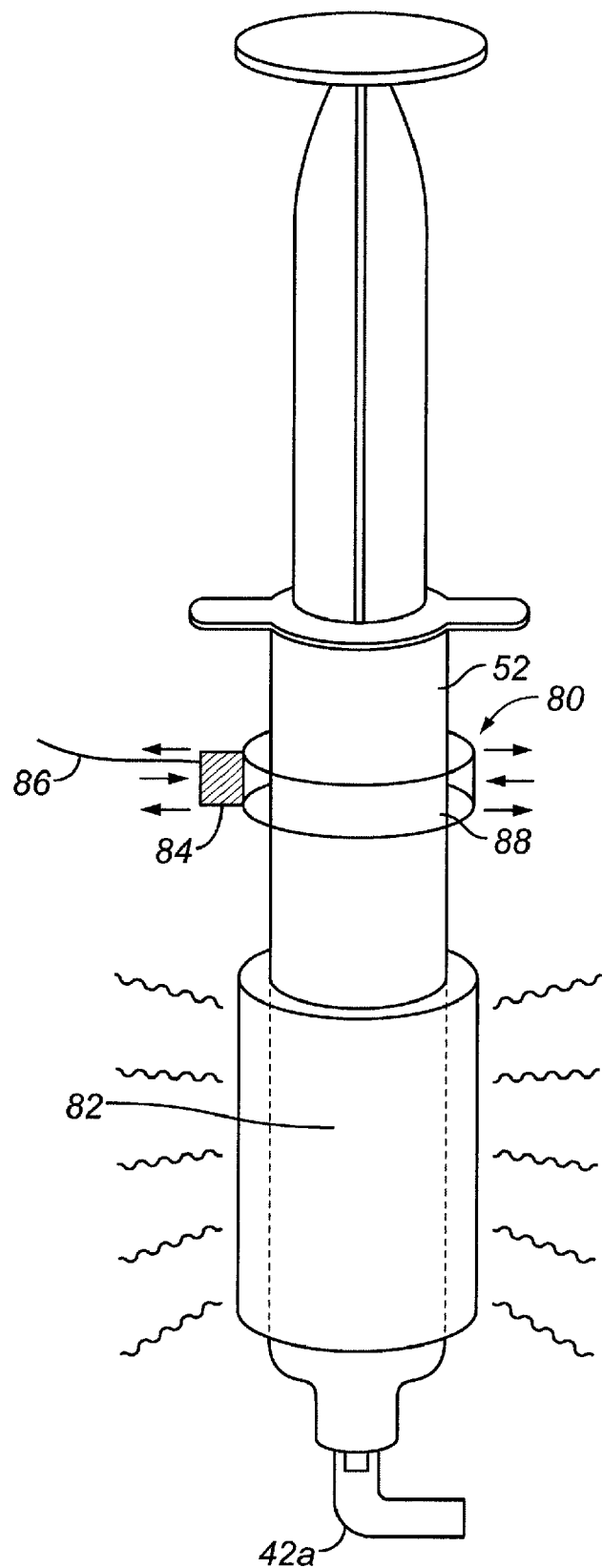
FIG. 6 shows an embodiment of a fill reservoir portion of the device of FIG. 1A including optional temperature control and mixing devices.

FIG. 6 shows an optional agitation device 80 and an optional temperature control device 82 that may, in some embodiments, be included to agitate (e.g., mix, shake, stir, swirl, move, spin, etc.) or otherwise prevent settling or separation of the one or more of the component substances and/or to control the temperature of one or more of the component substances. Such optional agitation device 80 and an optional temperature control device 82 will typically be attached or connected to an optional fill reservoir (e.g., fill syringes 52 and/or 54) but, in some cases, may be attached or connected to the component injectors (e.g., component injector syringes 16, 18). For example, in cases where the optional fill syringe 52 contains a thrombin containing component such as thrombin solution used in the delivery of PG or APG therapy, it may be desired to maintain the thrombin containing component at a desired temperature, for example at below room temperature. To accomplish this, an insulation material and/or a coolant device 82 (e.g., ice pack, endothermic reaction coolant, refrigeration unit, thermoelectric cooler, etc.) may be connected to, disposed on or otherwise associated with that fill syringe 52 (or other fill reservoir) containing the thrombin-containing component and/or with the component injector syringe 18 (or other injector) that contains the thrombin-containing component. It will be appreciated that, for other therapies, other types of temperature control or maintenance apparatus (including any suitable heating and/or cooling apparatus) may be used to provide a component substance that is warmed or cooled to a desired temperature.

Also, in such cases, the platelet-containing component may comprise a suspension of platelets (e.g., PRP is a suspension of platelets in plasma). As such, it may be desirable or necessary to maintain the platelets in a substantially homogenous suspension until the time of injection. In such instances, the object is to maintain the suspension of the platelets but not to agitate the PRP to the point where the platelets are damaged or sheared. To accomplish this, the entire injection device may be gently shaken or moved by hand or by mechanical means between doses of the therapy. Or, the device may optionally include an agitation device 80 for agitating (e.g., mixing, shaking, stirring, swirling, moving, spinning, etc.) at least those portions of the device that contain the platelet-containing component. For example, as seen in the example of FIG. 6, an agitation device 80 comprising a small vibrator 84 that is attached to the fill syringe 52 by an elastic band 88, may be used to gently agitate PRP contained within fill syringe 52 by vibrating the barrel of the syringe sufficiently to maintain the PRP in a homogenous suspension.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A device for administering a plurality of component substances into or onto the body of a human or animal subject such that the component substances become combined to produce a resultant component mixture or reaction product that directly or indirectly results in some therapeutic, diagnostic or cosmetic benefit, said device comprising:
    a manifold having a first component substance flow channel and a second component substance flow channel;
    a first injector connectable to the manifold and containing a first component substance, said first injector being usable to inject a first component substance into the first component substance flow channel of the manifold;
    a second injector connectable to the manifold and containing a second component substance, said second injector being usable to inject a second component substance into the second component substance flow channel of the manifold;
    an injector cannula assembly comprising;
    an outer tube that has an outer tube lumen and a distal opening, said outer tube being connected to the first component substance flow channel of the manifold such that the first component substance will flow through the outer tube lumen; and
    an inner tube that has an inner tube lumen and a distal opening, said inner tube being connected to the second component substance flow channel of the manifold such that the second component substance will flow therefrom into the inner tube lumen and out of the distal opening of the inner tube;
    a first reservoir containing an additional quantity of the first substance and being connected to the manifold so that the first component substance may pass from the first reservoir and into the first injector when it is desired to refill the first injector with first component substance;
    a second reservoir containing an additional quantity of the second substance and being connected to the manifold so that the second component substance may pass from the second reservoir and into the second injector when it is desired to refill the second injector with second component substance;
    a substance temperature control apparatus for controlling the temperature of at least one of the component substances while it is contained in the first reservoir or second reservoir;
    wherein at least a portion of the inner tube extends through at least a portion of the outer tube lumen such that the second component substance becomes combined with the first component substance thereby forming a resultant component substance mixture or reaction product; and
    wherein the device further comprises valving apparatus useable to alternately allow a) the first component substance to flow from the first reservoir into the first injector and the second component substance to flow from the second reservoir into the second injector and b) the first component substance to flow from the first injector into the outer tube lumen and the second component substance to flow from the second injector into the inner tube lumen.

2. A device according to claim 1 wherein the distal opening of the inner tube is located within the outer tube lumen such that the first and second component substances become combined within the outer tube lumen.

3. A device according to claim 1 wherein the distal end opening of the inner tube is located flush with or outside of the distal opening of the outer tube such that the first and second component substances become combined after exiting the distal openings of the inner and outer tubes.

4. A device according to claim 1 wherein a portion of the inner tube is substantially coaxially disposed within the outer tube lumen.

5. A device according to claim 1 further comprising a handle that facilitates holding of the device by a human operator, the handle being configured to hold the first and second injectors; and
    the handle further comprises a depressible member that, when depressed, causes substantially simultaneous injection of the first and second component substances from the first and second injectors.

6. A device according to claim 5 wherein the handle further comprises finger grips for receiving the operator's fingers while the operator's thumb is used to depress the depressible member and the handle is configured such that an operator can use the device with a one hand.

7. A system according to claim 5 wherein the first and second injectors have plungers which may be depressed to cause injection of the first and second component substances and wherein the depressible member engages the plungers of the first and second injectors and is usable to simultaneously depress those plungers at substantially the same rate.

8. A system according to claim 1 wherein the first injector and second injector differ in size.

9. A system according to claim 8 wherein the ratio of the volumes of the first injector and the second injector is approximately ten to one.

10. A device according to claim 1 further comprising apparatus for agitating at least one component substance.

11. A device according to claim 10 wherein the apparatus for agitating at least one component substance operates to agitate a substance while it is contained in either the first reservoir or second reservoir.

12. A device according to claim 1 wherein the injector cannula has a sharp tissue-penetrating distal end.

13. A device according to claim 1 further comprising a depth stop for limiting the depth to which the injector cannula may be advanced into tissue.

14. An injector device comprising:
at least one injector having a barrel into which a flowable substance may be loaded, an outlet opening and a plunger having a thumb pad that may be depressed by the thumb of a user to depress the plunger thereby causing a substance that has been loaded into the barrel to be expelled out of the outlet opening;
a first set of finger grips at a first location; and
a second set of finger grips at a second location longitudinally spaced from the first location;
the first and second sets of finger grips being configured such that a user may place two fingers of his or her hand under a selected one of the first and second sets of finger grips while the thumb of that hand is placed on the thumb pad and used to depress the plunger.

15. An injector device according to claim 14 wherein said at least one injector comprises:
a first injector having a barrel into which a first substance may be loaded, a first outlet opening and a first plunger that, when depressed, causes a first substance that has been loaded into the barrel of the first injector to be expelled out of the outlet opening of the first injector;
a second injector having a barrel into which a second substance may be loaded, a second outlet opening and a second plunger that, when depressed, causes a second substance that has been loaded into the barrel of the second injector to be expelled out of the outlet opening of the second injector;
a thumb-depressible member that engages both the first and second plungers so as to depress both the first and second plungers at substantially the same rate;
a manifold connected to the first and second injectors, said manifold having a first substance flow channel into which the first substance flows from the first injector and a second substance flow channel into which the second substance flows from the second injector; and
at least one cannula attached to the manifold.

16. A device according to claim 15 wherein said at least one cannula comprises a first cannula lumen through which the first substance flows and a second cannula lumen through which the second substance flows, and the first cannula lumen and the second cannula lumen are in biaxial relation to one another.

17. A device according to claim 15 wherein said at least one cannula comprises a cannula assembly that includes;
an outer tube that has an outer tube lumen and a distal opening, said outer tube being connected to the first substance flow channel of the manifold such that the first substance will flow through the outer tube lumen; and
an inner tube that has an inner tube lumen and a distal opening, said inner tube being connected to the second substance flow channel of the manifold such that the second substance will flow therefrom into the inner tube lumen and out of the distal opening of the inner tube; and
wherein at least a portion of the inner tube extends through at least a portion of the outer tube lumen such that the second substance becomes combined with the first substance thereby forming a resultant substance mixture or reaction product.

18. A device according to claim 17 wherein a portion of the inner tube is substantially coaxially disposed within the outer tube lumen.

19. A device according to claim 14 wherein said at least one injector comprises a syringe.

20. A device according to claim 15 further comprising:
a first fill reservoir for containment of a quantity of the first substance and a second fill reservoir for containment of a quantity of the second substance, the first fill reservoir being connected to the first injector and the second fill reservoir being connected to the second injector such that the first injector may be loaded with a quantity of the first substance from the first fill reservoir and the second injector may be loaded with a quantity of the second substance from the second fill reservoir, without requiring detachment of the first or second injectors from the manifold; and
a first valve and a second valve, each of said first and second valves being moveable between i) a first position whereby it allows a quantity of a substance to flow from a fill reservoir into an injector and ii) a second position whereby the substance may be injected from that injector without backflowing into the fill reservoir.

21. A device according to claim 20 wherein the first and second fill reservoirs comprise syringes.

22. A device according to claim 20 further comprising apparatus for controlling or maintaining the temperature of at least one of the substances while the at least one substance is contained in at least one of the first fill reservoir or the second fill reservoir.

23. A device according to claim 20 further comprising apparatus for agitating at least one of the substances while the at least one substance is contained in at least one of the first fill reservoir or the second fill reservoir.

24. A device according to claim 15 wherein said at least one cannula has a sharp tissue-penetrating distal end and a depth stop for limiting the depth to which the cannula may be advanced into tissue.

* * * * *